United States Patent
Scalzi et al.

(10) Patent No.: US 10,219,518 B2
(45) Date of Patent: *Mar. 5, 2019

(54) INHIBITION OF METHANOGENESIS TO CONTROL WOOD BORING INSECTS AND PESTILENCE

(71) Applicant: Environmental Intellectual Property, Inc, Pipersville, PA (US)

(72) Inventors: Michael Scalzi, Doylestown, PA (US); James Mueller, Freeport, IL (US); Antonis Karachalios, North Wales, PA (US)

(73) Assignee: Environmental Intellectual Property, Inc., Pipersville, PA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/269,903

(22) Filed: Sep. 19, 2016

(65) Prior Publication Data

US 2017/0079279 A1    Mar. 23, 2017

Related U.S. Application Data

(60) Provisional application No. 62/220,389, filed on Sep. 18, 2015.

(51) Int. Cl.
| | |
|---|---|
| *A01N 65/44* | (2009.01) |
| *A01N 63/04* | (2006.01) |
| *A01N 25/00* | (2006.01) |
| *A01N 37/06* | (2006.01) |
| *A01N 25/10* | (2006.01) |
| *A01N 25/12* | (2006.01) |
| *A01N 65/42* | (2009.01) |
| *A01N 65/24* | (2009.01) |

(52) U.S. Cl.
CPC .......... *A01N 63/04* (2013.01); *A01N 25/006* (2013.01); *A01N 25/10* (2013.01); *A01N 25/12* (2013.01); *A01N 37/06* (2013.01); *A01N 65/24* (2013.01); *A01N 65/42* (2013.01); *A01N 65/44* (2013.01)

(58) Field of Classification Search
None
See application file for complete search history.

(56) References Cited

U.S. PATENT DOCUMENTS

| | | |
|---|---|---|
| 5,592,774 A | 1/1997 | Galyon |
| 5,648,258 A | 7/1997 | Odom |
| 5,661,164 A | 8/1997 | Otsu |
| 5,756,114 A * | 5/1998 | Peterson .............. A01N 25/006 424/405 |
| 5,985,907 A | 11/1999 | Wolin |
| 6,374,536 B1 | 4/2002 | Washburn |
| 6,584,728 B2 | 7/2003 | Aesch |
| 6,681,518 B2 | 1/2004 | Aesch |
| 8,586,025 B2 | 11/2013 | Hatano |
| 2003/0167678 A1 | 9/2003 | Hunt |
| 2003/0219467 A1 * | 11/2003 | Miner .................. A61K 31/131 424/442 |
| 2009/0010979 A1 | 1/2009 | Baker |
| 2013/0217574 A1 * | 8/2013 | Reid ...................... A01N 43/40 504/118 |
| 2014/0242199 A1 * | 8/2014 | Manhas ................ A01N 25/02 424/736 |
| 2016/0045604 A1 * | 2/2016 | Pimentel .............. A61K 9/2846 514/460 |
| 2018/0001358 A1 * | 1/2018 | Scalzi ........................ B09C 1/08 |
| 2018/0093308 A1 * | 4/2018 | Mueller ..................... B09C 1/08 |

FOREIGN PATENT DOCUMENTS

| | | |
|---|---|---|
| CN | 1053558 C | 6/2000 |
| CN | 103829090 A | 6/2014 |

OTHER PUBLICATIONS

Prins R. et al. Pure Culture Studies of Inhibitors for Methanogenic Bacteria. Antonie van Leeuwenhoek 38:281-287, 1972. (Year: 1972).*
Crook, D. et al. Development of a Host Based Semiochemical Lure for Trapping Emerald Ash Borer. Chemical Ecology Environmental Entomology 37(2)356-365, 2008. (Year: 2008).*
Moawad S. et al. Behavioural Response of Anacanthotermes ochraceus Towards Some Baits and Volatile Oils. J of Agricultural Science and Technology B 2(12)1279-1286, 2012. (Year: 2012).*
Gottlieb, K., et al., "Inhibition of Methanogenic Archaea by Statins as a Targeted Management Strategy for Constipation and Related Disorders," AP&T 2016; 43: 197-212, John Wiley & Sons Ltd.
Reay, Dave, "Methane Sources—Termites," GreenHouse Gas Online, 2006, available at http://www.ghgonline.org/methanetermite.htm.
Hook, Sarah E., et al., "Methanogens: Methane Producers of the Rumen and Mitigation Strategies," Hindawi Pub. Co., Archaea, vol. 2010, Article ID 945785.

(Continued)

*Primary Examiner* — Ralph J Gitomer
(74) *Attorney, Agent, or Firm* — Douglas J. Ryder; Ryder, Mazzeo & Konieczny LLC

(57) ABSTRACT

A method for inhibiting methane production in the digestive tract of methanogenic Archaea (e.g., termites, other wood boring pests). The inhibiting of the critical biochemical pathways specific to the methanogenic Archaea is achieved by having the methanogenic Archaea ingest an anti-methanogenic compound. The anti-methanogenic compound may include, for example, naturally-occurring statins or derivatives thereof, linoleic acid or related compounds, essential oils, or some combination thereof. The naturally-occurring statins can be found in the red yeast rice extract or related biomass. As a result, the effectiveness of the methanogenic Archaea to produce methane is compromised, which subsequently results into the malfunctioning of the xylophages' digestive system. This provides a safe, natural, green and sustainable means of controlling many pests such as the Asian Beetle, Emerald Ash borer, Weevils, Deathwatch Caterpillars, and termites.

13 Claims, 13 Drawing Sheets

(56) References Cited

OTHER PUBLICATIONS

Johnson, Jane M. F., et al., "Agricultural Opportunities to Mitigate Greenhouse Gas Emissions," Elsevier Ltd., Environmental Pollution 150 (2007) 107-124.
Moss, Angela R., et al., "Methane Production by Ruminants: Its Contribution to Global Warming," INRA, EDP Sciences, Ann. Zootech. 49 (2000) 231-253.
Pester, Michael, et al., "Methane Oxidation in Termite Hindguts: Absence of Evidence and Evidence of Absence," Applied and Environmental Microbiology, vol. 3, No. 6, Mar. 2007, p. 2024-2028.
Velu, Gomati, "Green House Gas Emissions from Termite Ecosystem," Academic Journals, African Journal of Environmental Science and Technology vol. 5(2), pp. 56-64, Feb. 2011.
U.S. Environmental Protection Agency, "Overview of Greenhouse Gases: Methane Emissions," 2014, available at https://www.epa.gov/ghgemissions/overview-greenhouse-gases#methane.
Cook, S.F., "The Respiratory Gas Exchange in Termopsis Nevadensis," Marine Biological Laboratory, Biological Bulletin vol. 63, No. 2 (Oct. 1932), 246-257.
Bignell, David E., et al., "Termites as Mediators of Carbon Fluxes in Tropical Forest: Budgets for Carbon Dioxide and Methane Emissions," Forests and Insects, Ch. 8, Edited by A.D. Watt, et al., Chapman & Hall (1997), 109-134.
Busquet, M., et al., "Effect of Garlic Oil and Four of its Compounds on Rumen Microbial Fermentation," American Dairy Science Association, J. Dairy Sci. 88:4393-4404 (2005).
Brune, A., et al., "Microecology of the Termite Gut: Structure and Function on a Microscale," Elsevier Science Ltd., 2000, 3:263-269.
Gomathi, V., et al., "Methan Emission by Gut Symbionts of Termites," Academic Journal of Plant Sciences 2 (3): 189-194, 2009.
Fraser, G.R., et al., "Assessment of the Effects of Cinnamon Leaf Oil on Rumen Microbial Fermentation Using Two Continuous Culture Systems," American Dairy Science Association, J. Dairy Sci. 90:2315-2328 (2007).
Miller, Terry L., et al., "Inhibition of Growth of Methane-Producing Bacteria of the Ruminant Forestomach by Hydroxymethylglutaryl~SCoA Reductase Inhibitors," American Dairy Science Association, J. Dairy Sci. 84:1445-1448 (2001).
Morgavi, D.P., et al., "Microbial Ecosystem and Methanogenesis in Ruminants," The Animal Consortium, Animal (2010), 4:7,1024-1036.
Morvan, B., et al., "Quantitative Determination of H2-Utilizing Acetogenic and Sulfate-Reducing Bacteria and Methanogenic Archaea from Digestive Tract of Different Mammals," Springer-Verlag New York Inc., Current Microbiology, vol. 32 (1996), 129-133.
Sanderson, M.G., "Biomass of Termites and Their Emissions of Methane and Carbon Dioxide: A Global Database," American Geophysical Union, Global Biochemical Cycles, vol. 10, No. 4, 543-557, (1996).
Sharma, A., et al., "Structure modeling and inhibitor prediction of NADP oxidoreductase enzyme from Methanobrevibacter smithii," Biomedical Informatics, Bioinformation 6(1): 15-19 (2011).
Shinzato, N., et al., "Phylogenetic Diversity of Symbiotic Methanogens Living in the Hindgut of the Lower Termite Reticulitermes speratus Analyzed by PCR and In Situ Hybridization," Applied and Environmental Microbiology, vol. 65, No. 2, Feb. 1999, 837-840.

\* cited by examiner

|  | Methane Flux, Mt yr$^{-1}$ |  | Carbon Dioxide Flux, Gt yr$^{-1}$ |
| --- | --- | --- | --- |
| Zimmerman et al. [1982] | 150 | (75-310) | 50 |
| Rasmussen and Khalil [1983] | < 50 |  | ... |
| Collins and Wood [1984]$^a$ | 15 | (< 34) | 5 |
| Seiler et al. [1984] | 5 | (2-5) | 6$^b$ |
| Fraser et al. [1986] | 14 | (6-42) | ... |
| Rasmussen and Khalil [1987] | < 15 |  | ... |
| Cicerone and Oremland [1988] | 40 |  | ... |
| Khalil et al. [1990] | 12 | (2-20) | 4 |
| Judd et al. [1993] | 27 | (15-35) | ... |
| Martius et al. [1993] | 26 | (15-37) | ... |
| Hackstein and Stumm [1994] | 50.7 | (6-51)$^c$ | ... |
| Mugodo [1995] | 14 |  | ... |
| This work | 20 | (18-22) | 3.5 (2.8-4.2) |

The range of values about the above estimates are given in parentheses.

$^a$Derived by Khalil et al. [1990] from the data of Collins and Wood [1984] and Zimmerman et al. [1982].

$^b$Derived by Khalil et al. [1990] from the data of Seiler et al. [1984].

$^c$Four estimates were quoted by these authors: 5.6, 23.0, 8.5, and 50.7 Mt yr$^{-1}$.

FIG. 5

| Period | Gas Vol. (mL) | COD (mg/L) | pH | ORP (mV) | TDS (mg/L) |
|---|---|---|---|---|---|
| CONTROL | | | | | |
| Startup-Week 1 | 81 | 56 | 6.4 | -382 | 1,333 |
| Startup-Week 2 | 73 | 91 | 6.3 | -366 | 1,341 |
| Test-Week 1 | 75 | 61 | 6.2 | -389 | 1,338 |
| Test-Week 2 | 73 | 108 | 6.3 | -396 | 1,359 |
| TEST | | | | | |
| Startup-Week 1 | 79 | 72 | 6.2 | -385 | 1,344 |
| Startup-Week 2 | 75 | 83 | 6.2 | -388 | 1,365 |
| Test-Week 1 | 83 | 65 | 6.1 | -386 | 1,365 |
| Test-Week 2 | 73 | 97 | 6.4 | -387 | 1,347 |

FIG. 7

| Activity | Time (days) | Control (%) | Test (%) |
|---|---|---|---|
| dosed Test (60 mg/L) | 0 | 57 | 63 |
| | 2 | 61 | 47 |
| | 4 | 68 | 32 |
| | 6 | 59 | 29 |
| dosed Control (20 mg/L) | 7 | 68 | 13 |
| | 9 | 31 | 6 |
| | 11 | 31 | 0 |
| | 13 | 33 | 0 |
| | 15 | 8 | 0 |
| | 17 | 0 | 0 |

FIG. 8

| Time (days) | SF1 (no MIRYR) | SF1 (with 20% MIRYR) | SF2 (no MIRYR) | SF2 (with 10% MIRYR) |
|---|---|---|---|---|
| 0.5 | 1.0 | 0.0 | 1.0 | 0.0 |
| 1.5 | 1.0 | 2.0 | 7.0 | 8.0 |
| 5 | 5.0 | 5.0 | 9.0 | 5.0 |
| 12 | 1.39 | 0.79 | 0.94 | 0.86 |
| 19 | 3.217 | 1.40 | 2.685 | 2.023 |

SF: Sample Formulation

| TEST | TREATMENT TESTED |
|---|---|
| 1 | Baseline Control (manure and groundwater only) |
| 2 | 4% Garlic Oil |
| 3 | 4% Cinnamon Oil |
| 4 | 4% Lemon Grass Oil |
| 5 | 4% Cinnamon Bark (dry powder) |
| 6 | 10% Garlic Oil |
| 7 | 10% Cinnamon Oil |
| 8 | 10% Lemon Grass Oil |
| 9 | 10% Cinnamon Bark (dry powder) |

FIG. 11

| Vial # | Reagent Added Date | Reagent Added Amount (g) | Date Analyzed | Time Following Set-up (days) | Time Following Dosing (days) | Methane (mg/L) | pH | ORP (mv) |
|---|---|---|---|---|---|---|---|---|
| | | | Manure Slurry Added to Vials: 10/19/2015 | | | | | |
| Control #1 | 10/23/15 | --- | 10/26/2015 | 7 | 3 | 3,675 | 5.31 | -54 |
| GO 4% #1 | 10/23/15 | 0.776 | 10/26/2015 | 7 | 3 | 3,180 | 5.58 | -159 |
| CO 4% #1 dup | 10/23/15 | 0.799 | 10/26/2015 | 7 | 3 | 3,095 | 5.61 | -100 |
| LO 4% #1 | 10/23/15 | 0.799 | 10/26/2015 | 7 | 3 | 2,910 | 5.50 | -61 |
| CB 4% #1 | 10/23/15 | 0.798 | 10/26/2015 | 7 | 3 | 2,820 | 5.16 | -35 |
| GO 10% #1 | 10/23/15 | 1.951 | 10/26/2015 | 7 | 3 | 2,610 | 5.27 | -119 |
| CO 10% #1 | 10/23/15 | 2.001 | 10/26/2015 | 7 | 3 | 2,710 | 5.39 | -71 |
| LO 10% #1 dup | 10/23/15 | 2.013 | 10/26/2015 | 7 | 3 | 3,675 | 5.87 | -74 |
| CB 10% #1 | 10/23/15 | 2.001 | 10/26/2015 | 7 | 3 | 2,100 | 5.17 | -26 |

FIG. 12

| Vial # | Reagent Added | | Date Analyzed | Time Following Set-up (days) | Time Following Dosing (days) | Methane (ug/L) | pH | ORP (mv) |
|---|---|---|---|---|---|---|---|---|
| | Date | Amount (g) | | | | | | |
| | | | Manure Slurry Added to Vials: 10/19/2015 | | | | | |
| Control #2 | 10/23/15 | --- | 10/30/2015 | 11 | 7 | 6,140 | 5.18 | -62 |
| GO 4% #2 | 10/23/15 | 0.774 | 10/30/2015 | 11 | 7 | 2,445 | 5.27 | -169 |
| CO 4% #2 | 10/23/15 | 0.798 | 10/30/2015 | 11 | 7 | 3,180 | 5.57 | -122 |
| LO 4% #2 dup | 10/23/15 | 0.801 | 10/30/2015 | 11 | 7 | 3,285 | 5.19 | -73 |
| CB 4% #2 dup | 10/23/15 | 0.804 | 10/30/2015 | 11 | 7 | 2,145 | 4.96 | -45 |
| GO 10% #2 | 10/23/15 | 1.948 | 10/30/2015 | 11 | 7 | 2,520 | 5.08 | -163 |
| CO 10% #2 | 10/23/15 | 2.019 | 10/30/2015 | 11 | 7 | 2,530 | 5.43 | -113 |
| LO 10% #2 | 10/23/15 | 2.008 | 10/30/2015 | 11 | 7 | 3,560 | 5.54 | -96 |
| CB 10% #2 | 10/23/15 | 1.999 | 10/30/2015 | 11 | 7 | 4,400 | 5.54 | -43 |

FIG. 13

| Vial # | Reagent Added | | Date Analyzed | Time Following Set-up (days) | Time Following Dosing (days) | Methane (g/L) | pH | ORP (mv) |
|---|---|---|---|---|---|---|---|---|
| | Date | Amount (g) | | | | | | |
| Control #3 | 10/23/15 | --- | 11/4/2015 | 16 | 12 | 7,920 | 5.23 | -74 |
| GO 4% #3 | 10/23/15 | 0.778 | 11/4/2015 | 16 | 12 | 2,030 | 5.12 | -173 |
| CO 4% #3 | 10/23/15 | 0.812 | 11/4/2015 | 16 | 12 | 4,700 | 5.77 | -116 |
| LO 4% #3 | 10/23/15 | 0.808 | 11/4/2015 | 16 | 12 | 2,720 | 5.08 | -61 |
| CB 4% #3 | 10/23/15 | 0.802 | 11/4/2015 | 16 | 12 | 2,950 | 4.96 | -46 |
| GO 10% #3 | 10/23/15 | 1.946 | 11/4/2015 | 16 | 12 | 1,635 | 5.23 | -198 |
| CO 10% #3 | 10/23/15 | 2.017 | 11/4/2015 | 16 | 12 | 4,020 | 5.46 | -131 |
| LO 10% #3 | 10/23/15 | 2.004 | 11/4/2015 | 16 | 12 | 5,420 | 5.10 | -43 |
| CB 10% #3 dup | 10/23/15 | 1.999 | 11/4/2015 | 16 | 12 | 5,270 | 5.03 | -22 |

Manure Slurry Added to Vials: 10/19/2015

FIG. 14

INHIBITION OF METHANOGENESIS TO CONTROL WOOD BORING INSECTS AND PESTILENCE

BACKGROUND

Natural methane ($CH_4$) emissions have gained much attention over the past few decades due to the importance of methane as a potent greenhouse gas. Methane's lifetime in the atmosphere is much shorter than carbon dioxide ($CO_2$), but $CH_4$ is more efficient at trapping radiation than $CO_2$ (i.e., pound for pound, the comparative impact of $CH_4$ on climate change is over 20 times greater than $CO_2$ over a 100-year period). Methane is emitted by natural sources such as wetlands, as well as human activities such as leakage from natural gas systems and the raising of livestock. In 2012, $CH_4$ accounted for about 9% of all U.S. greenhouse gas emissions from human activities (http://epa.gov/climatechange/ghgemissions/gases/ch.4.html#content). Of the various sources for natural methane emissions identified, the wood-feeding termite group is arguably the most significant, to the point where termites have been reported to be the largest source of greenhouse gases (methane) emissions on the planet Earth.

Bacterial methanogenesis is a ubiquitous process in most anaerobic environments. There are three major substrates used by methanogens to produce methane: i) $CO_2$, ii) compounds containing a methyl group, or iii) acetate. The association of bacterial methanogenesis with anaerobic decomposition of organic matter in microbial habitats such as the intestinal tract of animals, sewage, sludge digester, muds of various aquatic habitat etc., has been well established. Thus, gas production commonly observed in nature is mainly the result of the growth of methanogens under specific energy sources that were formed as a result of microbial decomposition of organic matter.

Methanogens belong to the domain Archaea. The diversity of archaea found in the rumen of many organisms has been reviewed by many researchers. Most archaea identified in the rumen of animals belong to known methanogen clades with a predominance of *Methanobrevibacter* spp. The pooled data from several surveys show that the *Methanobrevibacter* clade accounts for nearly two-thirds of rumen archaea. The remaining one-third was composed, of roughly equal parts by phylotypes belonging to methanomicrobium and the rumen cluster C.

Most rumen methanogens do not contain cytochromes and although they are less efficient at obtaining energy through the production of methane than their cytochrome-containing relatives of the order methanosarcinales, they are better adapted to the environmental conditions prevailing in the rumen. They have a lower threshold for hydrogen ($H_2$) partial pressure, a faster doubling time, that can be as short as 1 h, and they have the potential to develop better at the mesophilic temperature and the near neutral pH of the rumen.

Termites are eusocial insects that belong to the order isoptera and play a major role in tropical ecosystem. Their basic food is plant matter, both living and dead. The main diet of most of the termite species consists of wood, foliage, humus or a mixture of these foods. It is not known whether isopteran have a significant role in rumen methanogenesis but methanogens attached to the gut epithelium have been described in termites, and in such a microaerobic environment they are capable of producing methane and reducing oxygen at the same time.

Termites are divided into two groups, i) lower termites, and ii) higher termites. Lower termites is a group of six evolutionary distinct termite families (the microbial community in the gut of phylogenetically lower termites) comprising both flagellated protists and prokaryotes. This group includes approximately 85% of all termite species that also harbors a dense and diverse population of gut prokaryotes that typically lack eukaryotic flagellated protists. Higher termites secrete their own digestive enzymes and are independent of gut microorganisms in their nutrition. The lower termites also possess this ability, but their production of cellulolytic enzymes is apparently inadequate. Hence, lower termites mostly depend on the activity of gut microorganisms for their nutrition, which are present in the hind gut region. Methanogens play a crucial role in this community of gut microbiota: if methanogens are disrupted or impeded the ecology of the system fails and the host organism will suffer.

Methanogenesis is an important component of microbial carbon metabolism in the hind gut termite digestive system. Methanogenic bacteria share physiological and biochemical characters such as ability to anaerobically oxidize hydrogen and reduce carbon dioxide to methane. One of the most fascinating nutritional symbioses exists between termites and their intestinal microflora: a symbiosis that permits termites to live by xylophagy, or the consumption of wood. The termite gut represents an excellent model of highly structured micro-environments. Apart from its natural role of conversion of woody and cellulosic substances into useful products of termite gut, microbiota contribute significantly to greenhouse gas effect through methane generation.

FIG. 1 illustrates a gut of a termite and reaction chains that are taking place therewithin. The adult termite gut consists of fore gut (which includes the crop and muscular gizzard), the tubular mid gut (which as in other insects is a key site for secretion of digestive enzymes and for absorption of soluble nutrients) and relatively, a voluminous hindgut (which is also a major site for digestion and for absorption of nutrients). The morphological diversity of the termite gut microbiota is remarkable and has been documented for both lower and higher termites. Although some bacteria colonize the foregut and midgut, the bulk of intestinal microbiota is found in the hindgut, especially in the paunch, which is, the region immediately posterior to the enteric valve. The hindgut compartments harbor the bulk of the intestinal microbiota. These tracts were initially considered as 'fermentation chambers' analogous to the rumen of sheep and cattle (e.g. anoxic environments for an anaerobic, oxygen-sensitive microbiota).

Researchers have reported that arthropod gut provides a suitable niche for microbial activity, but the nature of microflora and their distribution depended on the physico-chemical conditions like pH, redox potential and temperature of that region. Further research supported that the presence of large number of aerobic, facultative and anaerobic microflora showed that hindguts are a purely anoxic environment together with steep axial pH gradients in higher termites. Among the different physiochemical conditions, pH and redox potential are the important factors which determine the type of microflora in the gut, while the pH of the foregut and midgut is around neutrality, whereas the paunch, colon and rectum appear to be slightly acidic.

FIG. 2 identifies known reductive reactions that occur in the gut of the termites. The most important metabolic activities traditionally attributed to the gut microbiota are, first, hydrolysis of cellulose and hemicelluloses, second, fermentation of the depolymerization products to shortchain fatty acids, which are then resorbed by the host, and third, intestinal nitrogen cycling and dinitrogen fixation. In the phylogenetically lower termites, a large fraction of hindgut volume (up to one-third of the body weight of a termite) is occupied by anaerobic flagellates, which phagocytize and degrade the wood particles comminuted by the termite. The phylogenetically higher termites do not harbor flagellates within their gut. Instead, an acquisition of cellulases with the food (in case of the fungus-cultivating termites) or a host origin of the cellulolytic activities has been suggested.

FIG. 3 illustrates a carbohydrate metabolism in wood and litter feeding termites. Termites are good sources of wood degrading enzymes such as cellulase-free xylanase, laccases that are potentially involved in phenolic compounds degradation suitable for paper and pulp industry and glucosidases. The metagenomic analysis of hindgut microbiota of higher termite shows the presence of diverse endoxylanases, endoglucanases, phosphorylases, glucosidases, nitrogenases, enzymes for carbon dioxide reduction and enzymes used in new ways for producing lignocelluloses based biofuels production and acetate production. Daily hydrogen turnover rates were 9-33 $m^3$ $H_2$ per $m^3$ hindgut volume, corresponding with the 22-26% respiratory activity of the termites. This makes $H_2$ the central free intermediate during lignocellulose degradation and the termite gut, with its high rates of reductive acetogenesis, the smallest and most efficient natural bioreactor currently known.

Termites inhabit many different ecological regions, but they are concentrated primarily in tropical grasslands and forests. Symbiotic micro-organisms in the digestive tracts of termites (flagellate protozoa in lower termites and bacteria in higher termites) produce methane. Termites emit large quantities of methane, carbon dioxide and molecular hydrogen into the atmosphere. Significant studies have been performed on diversity, social structure, physiology and ecology of the termites as source of methane contributing to the sources of atmospheric greenhouse gas. Methane production by termites was first reported by Cook (1932) who observed the evolution of a gas from a species of termite.

FIG. 4 illustrates the results of studies showing large variations in amount of methane produced (in a termite's digestive track during the breakdown of cellulose by symbiotic micro-organisms) for different species. Research also found average methane production rates of 0.425 µg $CH_4$/termite/day for the lower termite species and 0.397 µg $CH_4$/termite/day for the higher termite families. Environmental conditions such as light levels, humidity, temperature, as well as carbon dioxide and oxygen presence play a key part in methane production. Termites prefer the absence of solar radiation, an immobile atmosphere, saturated or nearly saturated, relative humidity, high and stable temperatures and even elevated levels of carbon dioxide. Although termite populations are active in the middle latitude environments, the vast concentrations of mounds and nests are found in the lower latitude tropical forests, grasslands and savannahs of Africa, Asia, Australia and South America. It is estimated that these regions contribute approximately 80% of global termite emissions.

Researchers performed laboratory experiments using termite mounds under glass enclosures, with varying diet patterns and temperatures, while all other variables remained stable. It was found that the capacity of termites to produce methane varied from species to species, within groups from different mounds or nests of a particular species. But all species produced methane which indicates that methanogens are active components of their biology. The six different species studied produced methane at rates that ranged over more than two orders of magnitude. Raising the temperature by 5° C. within each species' caused a 30-110% increase in the measured methane emissions. Prior laboratory and field research seems to show that termites preferred temperatures in excess of 10° C. above the ambient air temperatures, determined by their geographical locations. A positive correlation between amounts of biomass consumed and methane emitted was observed, with the average being 3.2 mg $CH_4$ per gram of wood.

Methanogenic bacteria have been associated with protozoa in termites. Though methanogens are generally strict anaerobes, their metabolic responses to the presence of oxygen and their sensitivity to it vary with the species. *Methanobacterium* sp. was isolated from the termite hindgut. *Methanobrevibacter cuticulam* and *M. curvatus* were isolated from the hindgut of the termite *Reticulitermes flaviceps*. The presence of *M. arboriphilicus* and *Methanobacterium bryantii* in the guts of wood eating higher termites has also been reported.

Termite guts are the world's smallest bioreactors. The presence of carbohydrate-fermenting bacteria and protozoa, high levels of volatile fatty acids in the gut fluid and the occurrence of typical anaerobic activities such as homoacetogenesis and methanogenesis resemble the situation encountered in the rumen of sheep and cattle.

Methane is a metabolic end product in the hindgut of most termites. It has been estimated that these insects contribute approximately 2 to 4% to the global emissions of this important greenhouse gas. Methanogenic archaea, which are easily identified by their coenzyme $F_{420}$ autofluorescence, have been located in several microhabitats within the hindgut. Depending on the termite species, these organisms can be associated either with the hindgut wall or with filamentous prokaryotes attached to the latter, or they can occur as ectosymbionts or endosymbionts of certain intestinal flagellates.

FIG. 5 illustrates annual emissions of methane and carbon dioxide in the atmosphere by termites as calculated by various researchers. The annual emission rates of methane and carbon dioxide were estimated by researchers using the equation $P=C\Sigma_{i=1}^{n}A_iB_iF_i$ where, P is the annual emission of the trace gas (in grams), $A_i$ is the area of an ecological region (in square meters), $B_i$ is the biomass of termites in that region (in grams per square per square meter) and $F_i$ is the flux of the trace gas (in grams of gas per grams of termites per hour).

FIG. 6 illustrates a termites life cycle. As a xylophagous termite grows and develops, methanogens clearly play an integral role in the reproduction, growth, development and overall activity of the organism. The microbes play similar roles in the life-cycles of other wood-boring insects and cellulose consumers such as xylophagous beetles.

A series of termite control methods have been implemented historically with varying measurements of success. A brief description of those techniques is presented below.

Fumigation: Fumigation ("tenting") has been the only method used for over forty years which insures complete eradication of all drywood termites from a structure. The phase-out of methyl bromide in the U.S. has positioned sulfuryl fluoride as the leading gas fumigant. Fumigation is a highly technical procedure which involves surrounding the structure with a gas-tight tarpaulin, releasing the gas inside the seal, and aerating the fumigant after a set exposure time.

Heat: Heat treatments are used to eradicate drywood termites. During the heat treatment the infested area is cordoned off with polyethylene or vinyl sheets. Temperature probes are placed in the hardest-to-heat locations and heat is applied with a high-output propane heater. After a lethal target temperature is achieved, the area can be cooled quickly.

Cold: Excessive cold is primarily applied by using liquid nitrogen, which is pumped into the targeted area until the temperature drops to a level lethal to drywood termites. Temperature probes are used to insure that lethal temperatures are attained.

Wood Injection: Wood injection or "drill-and-treat" applications have been used since the 1920s to treat drywood termite infestations which are accessible and detectable. An insecticide is injected into small holes drilled through any wood surface into termite galleries delivering the treatment directly to the pest population. This is the simplest and most direct method of treatment. The amount of drilling required and the effectiveness of this treatment depend on the chemical used and the nature of the infestation. Most chemicals will remain active in the wood after treatment to thwart resurgent colonies.

Borates: Spray and foam applications of products containing boron salts are applied to raw, uncoated wood surfaces. Because penetration depths of borate solutions and depth of drywood termite galleries vary, injections into existing infestations are usually being performed.

Microwave: Microwave energy, applied to relatively small sections of infested wood, kills termites by heating them. Thermocouples are inserted into treated members to ensure that adequate microwave energy is delivered.

Electrocution: The probe of a hand-held "gun" is passed slowly over the infested wood surface and inserted directly into pellet "kick-out" holes. The high voltage and low current energy emitted by the probe electrocutes termites in the immediate application area. There is no way to measure a lethal dose at a given location in wood with this device. In some cases, holes must be drilled into wood and wires inserted to improve penetration.

The most common delivery methods for the targeted treatment methods are baits and sprays. The baits consist of paper, cardboard, or other palatable food, combined with a slow-acting substance lethal to termites. The bait must be "tasty" enough that termites will readily consume it, even in the presence of competing tree roots, stumps, woodpiles and structural wood.

If the bait kills too quickly, sick or dead termites may accumulate in the vicinity of the bait stations, increasing the chance of avoidance by other termites in the area. Delayed-action also enhances transmission of the lethal agent to other termites, including those that never fed on the bait. Entire colonies can be eliminated in this manner, although total colony elimination is not always necessary to afford structural protection. The lethal compounds could also be made into a spray for use on susceptible wood surfaces or surfaces exhibiting infestation where pests need to be controlled. It could also be used incorporated into a sugar solution.

BRIEF DESCRIPTION OF THE DRAWINGS

FIG. 5 illustrates the annual emissions of methane and carbon dioxide in the atmosphere by termites that have been calculated by various researchers.

FIG. 7 is a table that lists the volume of biogas production, pH values, and the concentrations of COD, ORP, and TDS measured in the Control and Test reactors during the studies.

FIG. 8 is a table that lists the methane content measured in the biogas generated in the reactors during the 17-day study period.

FIG. 11 is a table that defines the tests performed for different essential oils.

FIGS. 12-14 are tables showing the results of the FIG. 11 tests for the 3 time intervals (day 3, day 7 and day 12 respectively).

DETAILED DESCRIPTION

Figures 1, 2:
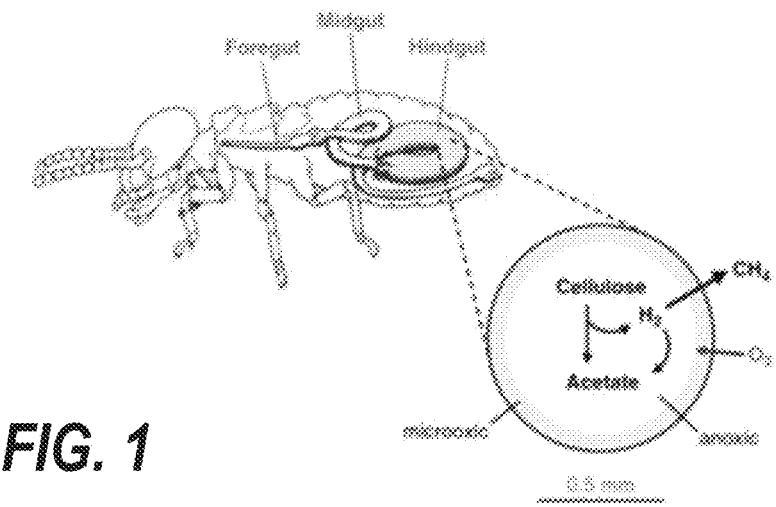
FIG. 1 illustrates a gut of a termite and reaction chains that are taking place therewithin.
FIG. 2 identifies known reductive reactions that occur in the gut of the termites.
Figure 3:
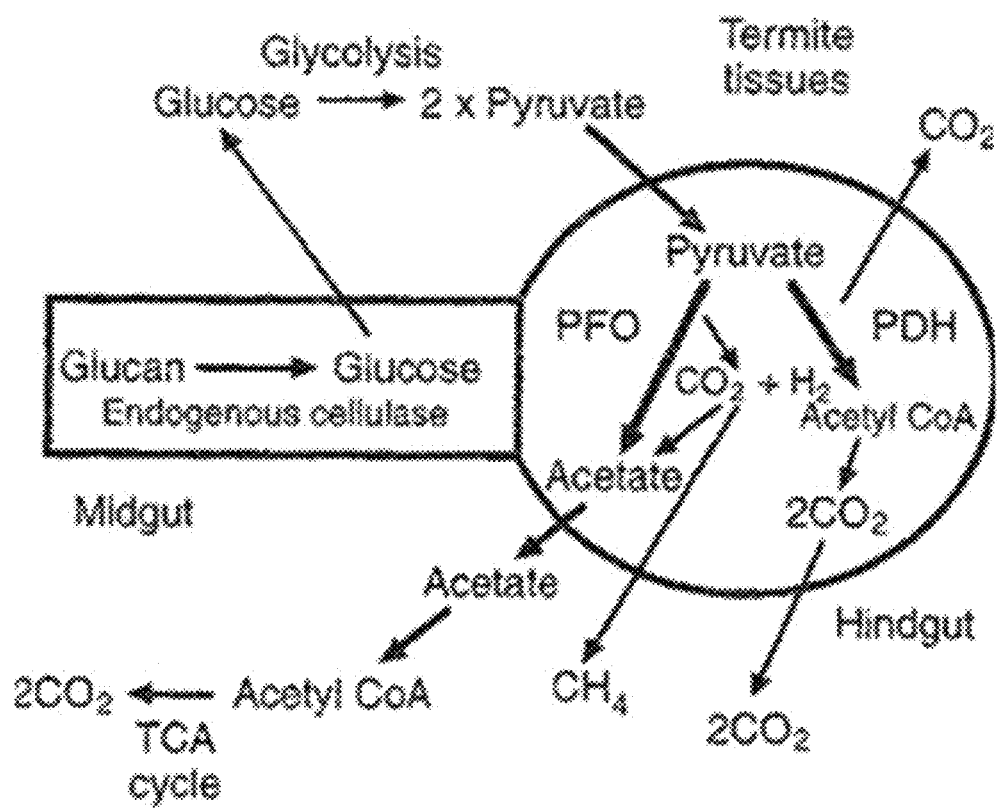
FIG. 3 illustrates a carbohydrate metabolism in wood and litter feeding termites.
Figure 4:
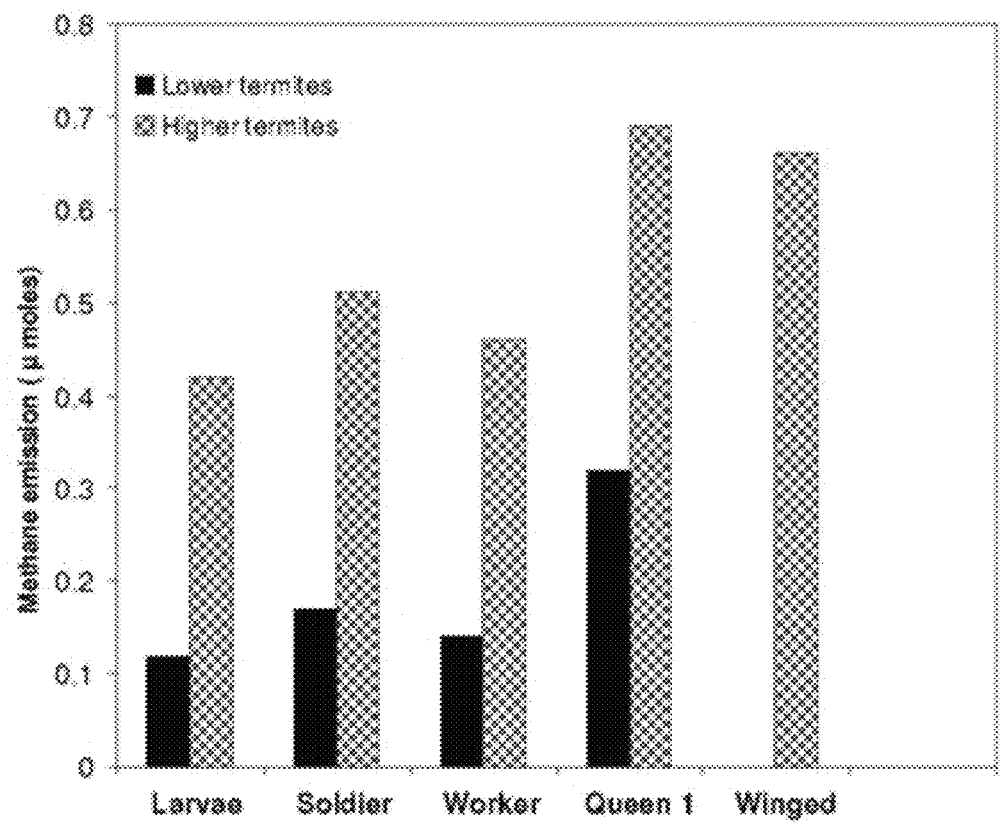
FIG. 4 illustrates the results of studies showing a large variations in amount of methane produced for different species.
Figure 6:
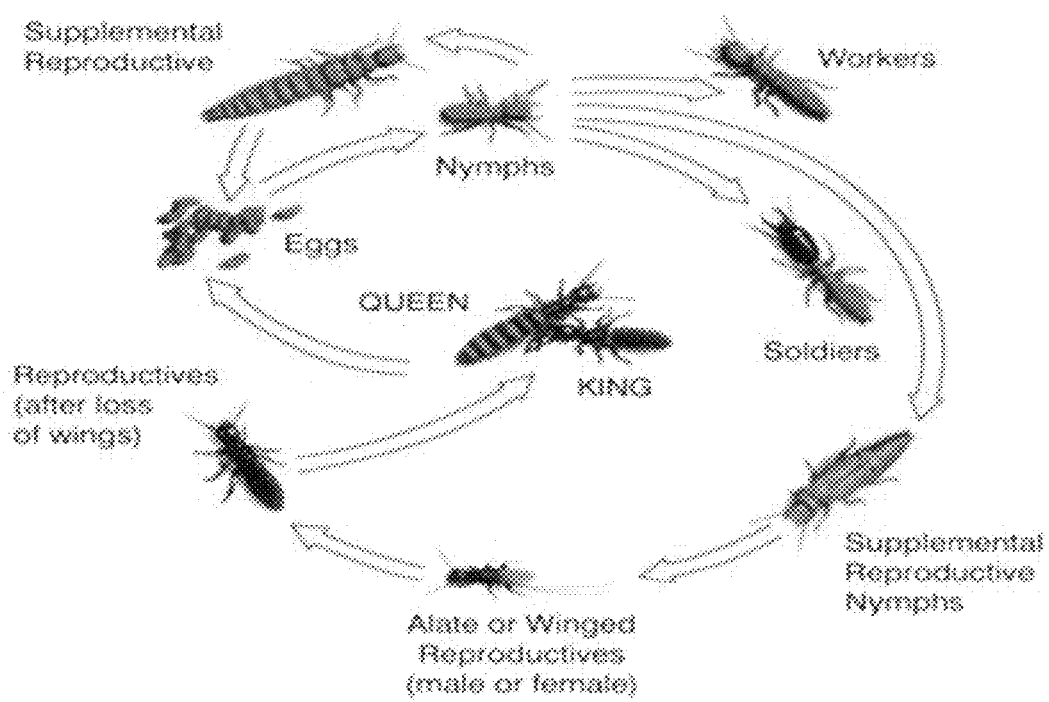
FIG. 6 illustrates a termites life cycle.

Methane fermentation is a versatile biotechnology capable of converting almost all types of polymeric materials to methane and carbon dioxide under anaerobic conditions. This is achieved as a result of the consecutive biochemical breakdown of polymers to methane and carbon dioxide in an environment in which a variety of microorganisms which include fermentative microbes (acidogens); hydrogen-producing, acetate-forming microbes (acetogens); and methane-producing microbes (methanogens) harmoniously grow and produce reduced end-products. Anaerobes play important roles in establishing a stable environment at various stages of methane fermentation.

The methanogenic *Archaea* (methanogens) occupy a variety of anaerobic habitats, where they play essential roles in the conversion of hydrogen and other intermediates to methane. Most species are capable of reducing carbon dioxide ($CO_2$) to a methyl group with either a molecular hydrogen ($H_2$) or formate as the reductant. Methane production pathways in methanogens that utilize $CO_2$ and $H_2$, involve specific methanogen enzymes, which catalyze unique reactions using unique coenzymes.

Several cofactors are involved in biological methane formation. Coenzyme B (HS-CoB, 7-mercaptoheptanoylthreonine phosphate) and coenzyme $F_{420}$ (a 5-deazaflavin derivative with a mild point potential of −360 mV) function as electron carriers in the process of methanogenesis. $F_{420}$ is the central electron carrier in the cytoplasm of methanogens, which replaces nicotinamide adenine dinucleotides in many reactions.

Methanogenesis from $H_2+CO_2$, formate, methylated $C_1$-compounds and acetate, proceeds by a central, and in most parts reversible pathway. When cells grow on $CO_2$ in the presence of molecular hydrogen, carbon dioxide is bound to methanofuran (MFR) and then reduced to formyl-MFR. This endogenic reaction is driven by the electrochemical ion gradient across the cytoplasmic membrane. In the next step the formyl group is transferred to $H_4MPT$ and the resulting formyl-$H_4MPT$ is stepwise reduced to methyl-$H_4MPT$. Reducing equivalents are derived from reduced $F_{420}$ ($F_{420}H_2$), which is produced by the $F_{420}$-reducing hydrogenase using hydrogen as a reductant. Furthermore, $F_{420}H_2$ is the electron donor for $F_{420}H_2$-dependent methylenetetrahydromethanopterin dehydrogenase (Mtd), one of two enzymes that reduce methenyl-H4MPT. The other enzyme, $H_2$-dependent methylenetetrahydromethanopterin dehydrogenase (Hmd), uses $H_2$ directly. mRNA abundance for mtd increased markedly under hydrogen-limited growth conditions, suggesting that Mtd may be more important when $H_2$ is limiting.

Sharma et al. (2011) determined a 3D model structure of the $F_{420}$-dependent NADP oxidoreductase enzyme from *M. smithii*. Based on their protein model, they detected that these residues are making a ligand binding site pocket, and they found that ligand $F_{420}$ binds at the protein cavity. The inhibitor compounds lovastatin and compactin (mevastatin) show more affinity for the model protein as compare to the natural ligand $F_{420}$. They share the same cavity as by $F_{420}$ and surround by similar residues. Therefore, the inhibitor compounds lovastatin and compactin (mevastatin) were very effective in blocking the activity site for methane production since the enzyme was unable to bind with the substrate, resulting in decreased methane production.

Monacolin K, as an example statin, can also inhibit methanogenic archaea because cell membrane production in archaea shares a similar pathway with cholesterol biosynthesis (Miller and Wolin, 2001). More specifically, bacterial cell walls are predominantly comprised of murein (peptidoglycan). Archaea, however, do not produce murein; rather, their cell walls are composed of various sulfated-heteropolysaccharides, proteins and glycoproteins/lipids along with pseudomurein—a structural analogue of murein—which is biosynthesized via activity similar to that of HMG-CoA reductase which yields cholesterol in humans.

In the presence of a statin, HMG-CoA reductase is inhibited, pseudomurein biosynthesis pathway is interrupted, and methanogens are restricted from growth and proliferation. And since methanogens are so uniquely different than bacteria, the inhibitory effect of statins is not observed in microbes.

The compound 3-hydroxy-3-methylglutaryl coenzyme A (HMG-CoA) reductase, is another enzyme that is very critical in methane production, and *Archaea* are the only bacteria known to possess biosynthetic HMG-CoA reductase (Miller and Wollin, 2001). Garlic oil has been hypothesized to inhibit the biosynthesis of HMG-CoA (Busquet et al., 2005; Fraser et al, 2007). At higher concentrations, various essential oils have exhibited wider range anti-microbial activity so the dosage and applications strategies are wide and variable.

Anti-methanogenic compounds are compounds designed to inhibit methane production in environments where methanogens are established and active. It is believed that anti-methanogenic compounds could inhibit the methane production in the gut of termites and other wood-boring and cellulose digesting pests. Limiting the production of methane causes dysfunctioning of the pests' digestive system thus impeding their growth and development. The impediment of their growth and development would thus make this an effective non-toxic method of controlling termites and other similar pests.

Anti-methanogenic compounds may include one or more unique compounds that either alone or in combination with one another effect the production of methane. Red yeast rice is believed to be an anti-methanogenic compound. In order to determine the effectiveness of red yeast rice for inhibiting methane, two bench scale studies were performed.

Laboratory Study 1

Two anaerobic reactors were utilized, a control and a test reactor. The two reactors were seeded with biomass treating expired dietary supplement, which contained an active methanogenic population. The reactors were fed once per week, and were operated as anaerobic sequencing batch reactors.

During the first week of startup, the reactors contained only the methanogenic culture, without soil. After one week, silty sand was added, resulting in a slurry having a solids concentration of 20% by weight. The reactors were operated for another week with the silty sand, to ensure that the sand did not affect methanogenic activity. The bioreactors were 2.5 L in volume, containing 2 L of slurry. The reactors were airtight and were especially designed for anaerobic reactions. The reactors were maintained at laboratory temperature 22° C.-24° C. The reactors were operated by feeding with dietary supplement once a week. The target initial chemical oxidation demand ("COD") concentration after feeding was 2000 mg/L.

Throughout the week, the volume of biogas produced was measured as follows. A syringe was inserted periodically into a septum-filled port in the top of the reactor to collect a gas sample for methane content. The methane content of the biogas samples was then quantified by injecting into a gas chromatograph with a flame ionization detector (GC-FID). The reactors had dedicated probes to measure pH and oxidation reduction potential ("ORP"). After each cycle (i.e., before feeding), a probe was inserted into the reactor to measure total dissolved solids ("TDS"), and a sample was collected to measure COD. The mixer was turned off during sampling and feeding to minimize the introduction of oxygen into the reactor contents.

The test reactor was initially dosed with a 40 g/L concentration of red yeast rice. One week later the control was dosed with 20 mg/L red yeast rice.

Laboratory Study 2

Two test aliquots were prepared under a nitrogen atmosphere in a glove box as follows: (1) a 240 mL amber glass screw-cap septum bottle was filled with 100 g of dry soil (~70 mL); (2) deoxygenated deionized water was slowly added to the soil to saturate the soil; an additional 40 mL of water was then added to the soil; and (3) manure slurry was added to yield a 1 weight percent manure dose to the soil.

Once the bottle was sealed it was removed from the glove box. The soil was kept in the dark (by wrapping with foil) at room temperature (~22° C.). A needle connected to a polyethylene tube was pushed through the bottle septum and the tube outlet was placed in an inverted graduated cylinder in a water bath. The gas generation rate was recorded as the water was displaced over a period of 10 days.

The methane reduction trial included two sample formulations, with and without red yeast rice, for a total of 4 samples. The bottles were sampled 0.5, 1.5, 5, 12, and 19 days following the sample preparation.

Results for Laboratory Study 1

The first two weeks of the studies were the startup period, and the second two weeks were the test period. The startup period established the methanogenic population in the two reactors. During the first week of startup, the reactors were operated without the silty sand, and the second week they were operated with the silty sand (20% by weight). The test period started with the dosing of the test reactor with red yeast rice (40 g/L). During the first week of the test period the control was maintained as a proper control, with no red yeast rice added. Because the 40 mg/L dose of red yeast rice reduced methane production in the test reactor, it was decided to dose the control reactor with 20 g/L of red yeast rice during the second week of the test period. The test period lasted 17 days.

FIG. 7 is a table that lists the volume of biogas production, pH values, and the concentrations of COD, ORP, and TDS measured in the control and test reactors during the studies. The volume of biogas produced each feed cycle (i.e., each week) in the reactors ranged between 72-82 mL. It is notable that the volume of gas was not affected by the introduction of silty sand during week 2 of the startup period. The addition of 40 mg/L of red yeast rice to the test in the first week of the test period and the addition of 20 mg/L of red yeast rice during the second week of the test period did not appreciably impact biogas volume in the reactors. The COD measurements after each sequencing batch reactor cycle ranged from 56 to 108 mg/L. The reactors were fed 2000 mg/L each cycle, so the COD concentrations in FIG. 7 demonstrate that the COD was consumed by the anaerobic culture. Values of pH ranged between 6.1 and 6.4. Values of ORP were all close to −300 mV, which is typical of methanogenic conditions. The TDS in the reactors ranged from approximately 1200 to 1250 mg/L.

FIG. 8 is a table that lists the methane content measured in the biogas generated in the reactors during the 17-day test period.

Figures 9, 10:
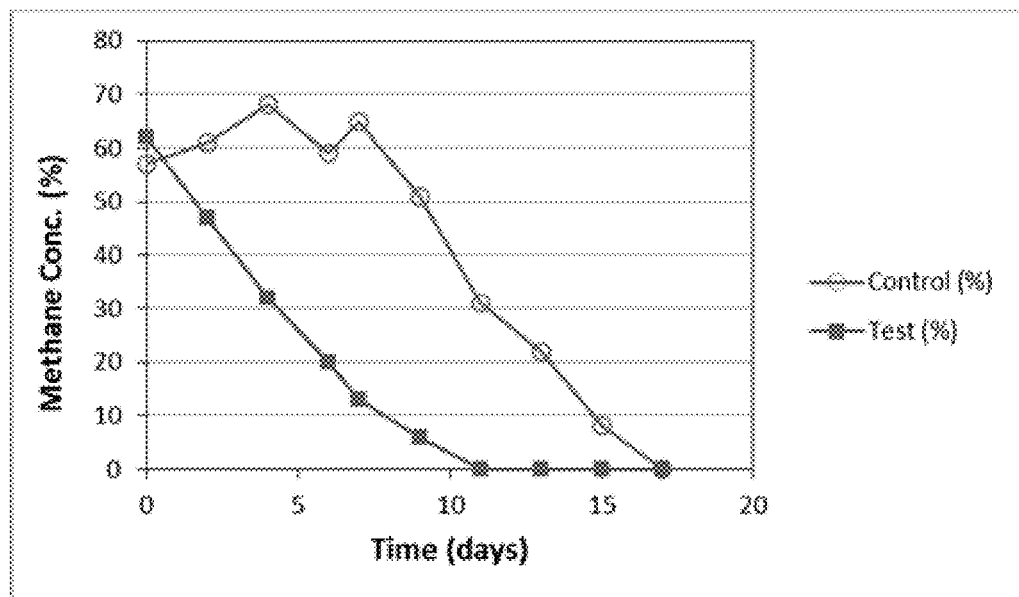
FIG. 9 is a graph of the methane concentrations listed in FIG. 8.
FIG. 10 is a table that lists the methane content measured in the biogas generated in the reactors during the 19-day study period.

FIG. 9 is a graph of the methane concentrations listed in FIG. 8. During the Startup Period, methane concentrations varied from approximately 55% to 70%, which indicates an active methanogenic culture. The red yeast rice dose of 40 mg/L in the Test reactor reduced the methane content of biogas from 62% to below detection (0.05%) after 11 days. The methane concentration remained below detect in the Test reactor until day 17, when the reactors were dismantled. The red yeast rice dose of 20 mg/L in the Control reactor on day 7 reduced the methane content of biogas from 65% to below detection (0.05%) by day 17 (i.e., after 10 days). During the Test period, the volume of biogas produced in the Test and Control reactors did not change appreciably only the methane concentration of the biogas was changed.

Results for Laboratory Study 2

FIG. 10 is a table that lists the methane content measured in the biogas generated in the reactors during the 19-day study period. The first soil formulation (SF1) that contains 20% of the red yeast rice (approximately 40 mg/L in solution) showed great effectiveness in inhibiting the methane production by 96% during the 19-day sampling interval. Similarly at the same time fragment the second soil formulation (SF2) resulted into a 25% decrease in methane production.

The above tests clearly illustrate the effectiveness of red yeast rice in inhibiting methane. By contacting the termites with red yeast rice (e.g., having the termites digest the red yeast rice) it is believed that this would provide a green, organic and non-toxic (to humans) way to control damage and pestilence induced by wood-boring insects that harbor methanogens in order to digest or metabolize cellulose.

Utilizing organic statins (some of which can be present in red yeast rice extract as well as biomass of other organisms) may inhibit the methanogenic enzyme and coenzyme systems essential to the growth and development of wood-boring insects. Thus disrupting their digestive tracts/life-cycle stages by limiting their effectiveness in producing methane and causing dysfunctioning of the pests' digestive system thus impeding their growth and development.

Essential oils are also believed to be an anti-methanogenic compound. Laboratory studies were performed to comparatively evaluate the anti-methanogenic potential of multiple essential oils (e.g., Garlic Oil [GO], Cinnamon Bark Oil [CO], Cinnamon Bark Powder containing 4% CO [CB] and lemongrass Oil [LO]).

Laboratory Study 3

Manure and groundwater samples were collected from a site in Monticello, Wis. at 1:1 ratio. The collected samples were added to 125 mL amber glass bottles equipped with PTFE-lined open septum caps (VOA vials). The testing program included 40 vials each filled with 20 g manure slurry and 20 g groundwater. All samples were sacrificial and disposed after completion of the analyses. Five (5) vials were used to indicate the onset of anaerobic conditions by measuring pH, ORP and methane over a 2-week period.

FIG. 11 is a table that defines the tests performed. A total of 27 vials were prepared to analyze the 9 tests defined in FIG. 11 over 3 time intervals (day 3, day 7, day 12). Finally 8 vials were setup as replicate samples.

Gas samples from the sample container headspace were analyzed for methane in the gas phase using a gas chromatograph (GC) with a flame ionization detector (FID). After these analyses were completed, pH and ORP were also measured.

Figure 15:
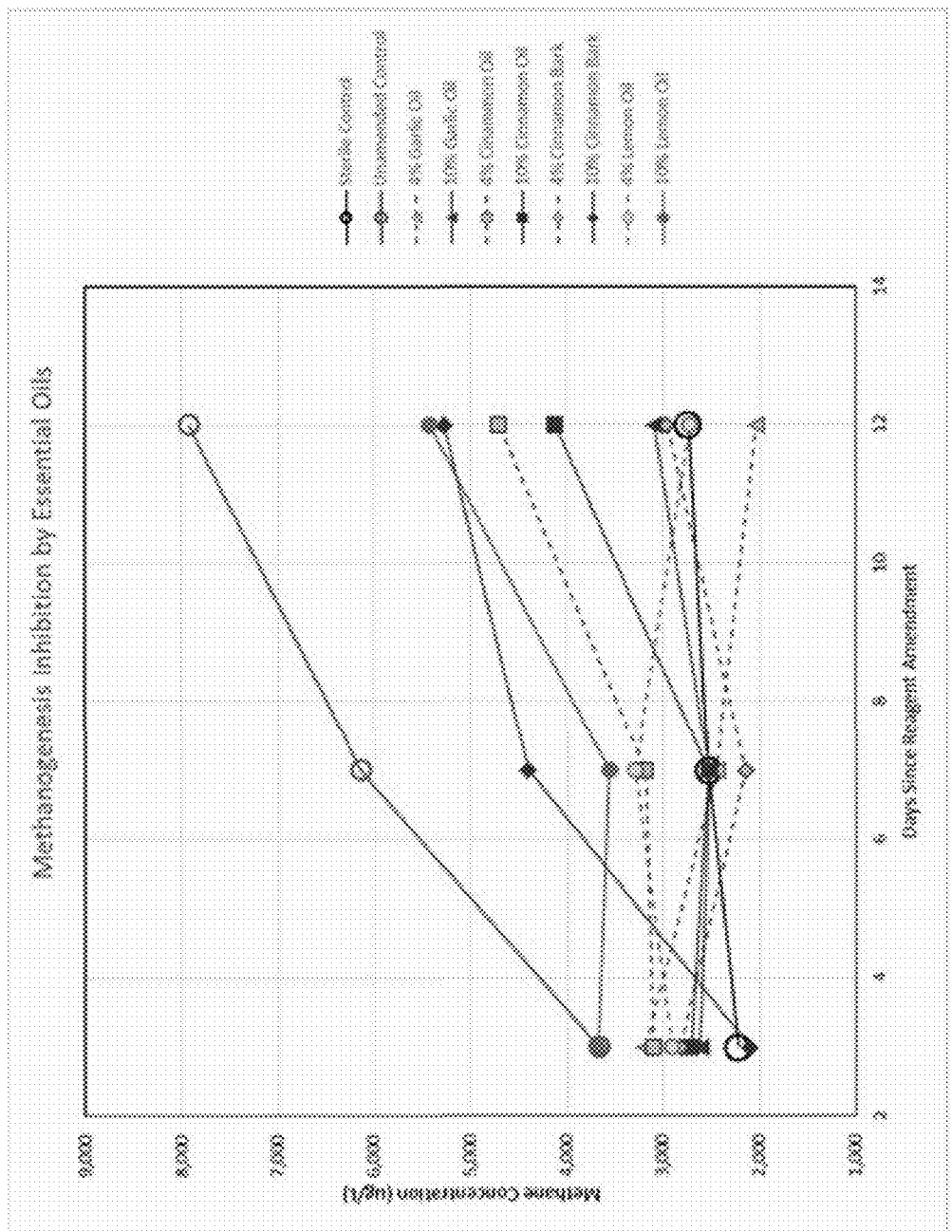
FIG. 15 is a graph showing the results for the tests of FIG. 11 for the different time intervals.

FIGS. 12-14 are tables showing the results of the 9 tests for the 3 time intervals (day 3, day 7 and day 12 respectively). FIG. 15 is a graph showing the results for all the tests for the different time intervals. As illustrated, it is apparent that all essential oils were successful in decreasing the amount of methane produced, with the Garlic Oil [GO] appearing to be the most effective of all.

As a termite xylophagous termite grows and develops, methanogens clearly play an integral role in the reproduction, growth, development and overall activity of the organism. The microbes play similar roles in the life-cycles of other wood-boring insects and cellulose consumers such as xylophagous beetles. As such, the anti-methanogenic compounds (e.g., red yeast rice, essential oils) could be utilized to control termites and all other wood-boring and cellulose digesting pests including but not limited to: i) the Emerald Ash Borer, ii) weevils, iii) wood-boring caterpillars (*Lepidoptera*) such as Carpenterworms (*Prionoxystus robinae*), and iv) wood-boring *Bostrichidae* beetles (formerly referred to as the family *Lyctidae*). The socioeconomic cost and destruction caused by such organisms is significant, and a means to control them using safe, natural, sustainable means is of great benefit to society.

The anti-methanogenic materials, described herein, can be applied in a myriad of ways (feed baits, aerial applications, dustings, coatings, pellets, powders) at various stages of the targeted organisms life cycle to yield effective treatment under various scenarios. The feed baits, aerial applications, dustings, coatings, pellets, and/or powders could be applied to locations where the pests are known to inhabit or feed. According to one embodiment, the anti-methanogenic compound is incorporated into cellulose based building materials.

Figure 16:
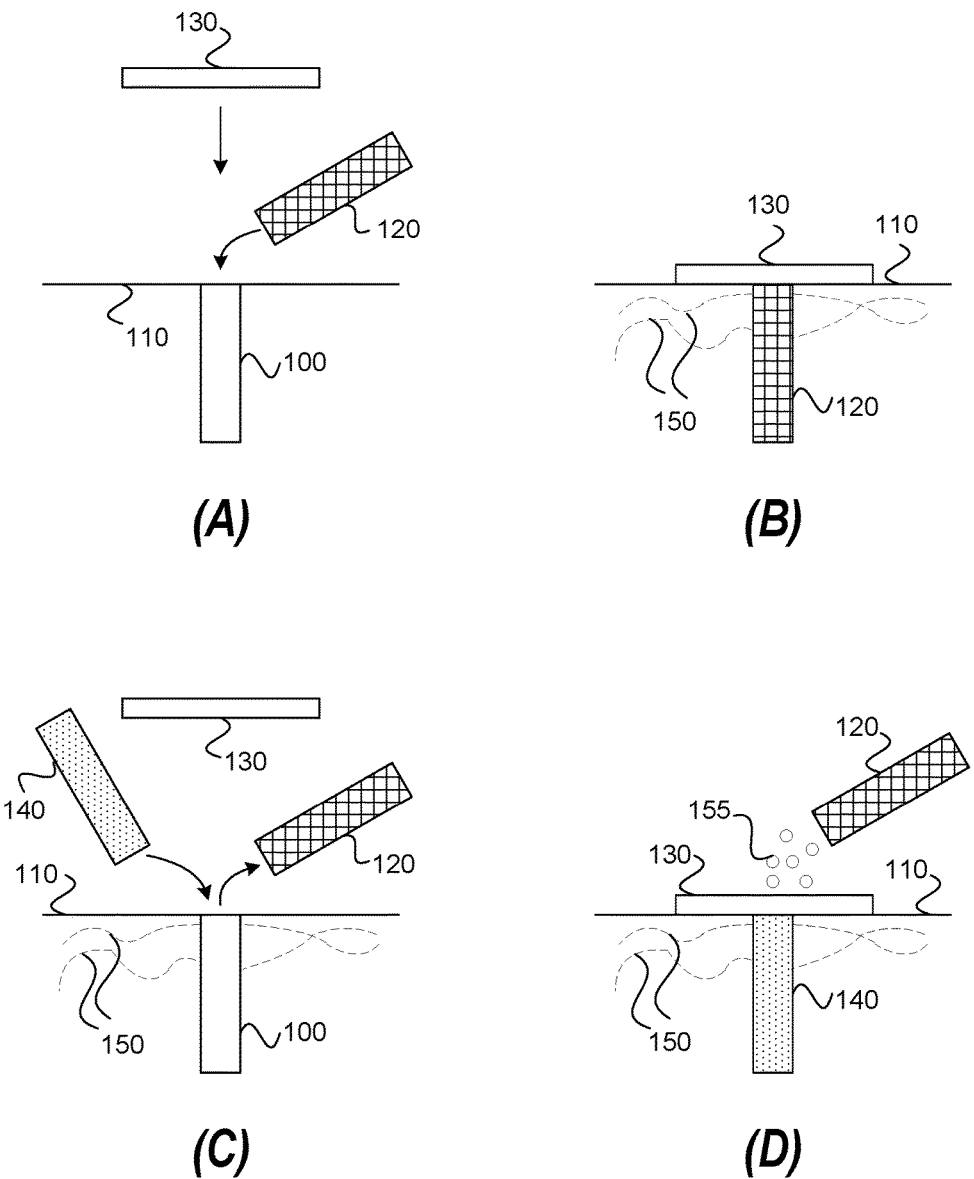
FIG. 16 illustrates an example feed bait process. The process starts in (A) where a bait station 100 is located in the ground 110. A monitoring device 120 is then paced into the ground 110 within the bait station 100. A station cover 130 is then placed on top. The process then flows to (B) where termites discover and occupy the monitoring device 120 in the bait station 100. The paths that the termites follow to get to the monitoring device 120 are illustrated as 150. The process then continues in (C) where the monitoring device 120 is removed and replaced with bait 140. The termites 155 from the monitoring device 120 are then placed on the bait 140 in the bait station 100 as illustrated in (D).

FIG. 16 illustrates an example feed bait process.

By controlling the activity of methanogens as disclosed, this provides a unique and important means of pest management.

It is understood that the invention is not limited to the disclosed embodiments and examples, but is intended to cover various modifications and equivalent arrangements included within the spirit and scope of the appended claims.

What is claimed is:

1. A method for disrupting digestive processes, communication methods and life-cycle of wood boring insects, the method comprising:

inhibiting methanogenic microbial population within the wood boring insects' gut by having the wood boring insects' ingest an anti-methanogenic compound including one or more naturally-occurring statins or derivatives thereof.

2. The method of claim 1, wherein the wood boring insects include termites, Emerald Ash Borers, beetles, and ants.

3. The method of claim 1, wherein the anti-methanogenic compound includes red yeast rice to provide the one or more naturally-occurring statins.

4. The method of claim 1, wherein the anti-methanogenic compound is incorporated into a wood boring insect "bait".

5. The method of claim 1, wherein the anti-methanogenic compound is incorporated into cellulose based building materials.

6. The method of claim 1, wherein the anti-methanogenic compound is incorporated into a spray.

7. The method of claim 1, wherein the anti-methanogenic compound is incorporated into a cellulose-based powder.

8. The method of claim 1, wherein the anti-methanogenic compound is combined or used individually with species and/or behavior specific pheromones.

9. A method for disrupting digestive processes, communication methods and life-cycle of wood boring insects, the method comprising:

providing a food source for the wood boring insects that includes an anti-methanogenic compound, wherein the anti-methanogenic compound includes red yeast rice and inhibits methanogenic microbial population within the wood boring insects' gut.

10. The method of claim 9, wherein the red yeast rice is to provide one or more naturally-occurring statins.

11. The method of claim 9, wherein the providing a food source includes at least some combination of providing a wood boring insect "bait", incorporating the anti-methanogenic compound into cellulose based building materials, incorporating the anti-methanogenic compound into a spray that is applied to the wood boring insects food source, and incorporating the anti-methanogenic compound into a cellulose-based powder that is applied to the wood boring insects food source.

12. The method of claim 9, wherein the anti-methanogenic compound is combined or used individually with species and/or behavior specific pheromones.

13. The method of claim 9, wherein the wood boring insects include termites, Emerald Ash Borers, beetles, and ants.

* * * * *